United States Patent
Yamakawa et al.

(10) Patent No.: US 9,675,288 B2
(45) Date of Patent: Jun. 13, 2017

(54) APPARATUS HAVING SURFACE-ENHANCED SPECTROSCOPY ELEMENTS ON AN EXTERIOR SURFACE

(71) Applicant: Hewlett-Packard Development Company, L.P., Houston, TX (US)

(72) Inventors: Mineo Yamakawa, Palo Alto, CA (US); Zhiyong Li, Palo Alto, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/764,528

(22) PCT Filed: Jan. 29, 2013

(86) PCT No.: PCT/US2013/023660
§ 371 (c)(1),
(2) Date: Jul. 29, 2015

(87) PCT Pub. No.: WO2014/120129
PCT Pub. Date: Aug. 7, 2014

(65) Prior Publication Data
US 2015/0374268 A1 Dec. 31, 2015

(51) Int. Cl.
*B01L 3/00* (2006.01)
*A61B 5/1459* (2006.01)
*G01N 21/65* (2006.01)
*A61B 5/00* (2006.01)
*G01N 21/25* (2006.01)

(52) U.S. Cl.
CPC .......... *A61B 5/1459* (2013.01); *A61B 5/6848* (2013.01); *G01N 21/658* (2013.01); *A61B 2562/0238* (2013.01); *A61B 2562/12* (2013.01); *G01N 2021/258* (2013.01); *G01N 2201/061* (2013.01); *G01N 2201/068* (2013.01)

(58) Field of Classification Search
CPC ............................ A61B 5/1459; G01N 21/658
See application file for complete search history.

(56) References Cited

U.S. PATENT DOCUMENTS

| 4,900,381 A | 2/1990 | Guenther et al. |
| 5,864,397 A | 1/1999 | Vo-Dinh |

(Continued)

FOREIGN PATENT DOCUMENTS

| CN | 102512181 A | 6/2012 |
| CN | 102525421 A | 7/2012 |

(Continued)

OTHER PUBLICATIONS

European Supplementary Search Report, Oct. 28, 2015, EP Patent Application No. 13873629.3, 3 pages.

(Continued)

*Primary Examiner* — Jyoti Nagpaul
(74) *Attorney, Agent, or Firm* — Mannava & Kang, P.C.

(57) ABSTRACT

According to an example, an apparatus for performing spectroscopy includes an elongated substrate having a shape and size to be inserted into a specimen, wherein the elongated substrate has a first end and a second end. The apparatus also includes a plurality of surface-enhanced spectroscopy (SES) elements positioned on an exterior surface of the elongated substrate at a location between the first end and the second end of the elongated substrate.

15 Claims, 5 Drawing Sheets

(56) References Cited

U.S. PATENT DOCUMENTS

| | | | |
|---|---|---|---|
| 7,236,242 B2* | 6/2007 | Kamins | G01N 21/658 356/301 |
| 7,333,206 B2 | 2/2008 | Clark | |
| 7,609,378 B2* | 10/2009 | Konakahara | G01N 21/658 356/301 |
| 8,243,270 B2* | 8/2012 | Kuo | G01J 3/44 356/301 |
| 8,314,932 B2* | 11/2012 | Ou | G01N 21/658 356/301 |
| 9,019,495 B2* | 4/2015 | Kim | G01N 21/658 356/301 |
| 2003/0135161 A1 | 7/2003 | Fleming et al. | |
| 2005/0055039 A1 | 3/2005 | Burnett et al. | |
| 2010/0129623 A1 | 5/2010 | Johansson et al. | |
| 2010/0182607 A1 | 7/2010 | Chau et al. | |
| 2011/0165077 A1 | 7/2011 | Qian et al. | |
| 2011/0165586 A1 | 7/2011 | Kim et al. | |
| 2011/0177530 A1 | 7/2011 | Corcoran et al. | |
| 2012/0092660 A1 | 4/2012 | Wu et al. | |
| 2012/0100560 A1 | 4/2012 | Searson et al. | |
| 2012/0281212 A1 | 11/2012 | Fattal et al. | |
| 2013/0230660 A1 | 9/2013 | Hase et al. | |

FOREIGN PATENT DOCUMENTS

| | | |
|---|---|---|
| CN | 102551674 A | 7/2012 |
| EP | 0279004 | 8/1988 |
| EP | 1465698 | 1/2008 |
| EP | 2615059 | 7/2013 |
| JP | S63212332 | 9/1988 |
| JP | 2005514179 | 5/2005 |
| JP | 2012196457 | 10/2012 |
| JP | 2012225719 | 11/2012 |
| TW | 201028678 A | 8/2010 |
| TW | 201245677 A | 11/2012 |
| WO | WO-03059431 | 7/2003 |
| WO | WO-2012033097 | 3/2012 |
| WO | WO-2012054027 | 4/2012 |
| WO | WO-2012128773 | 9/2012 |
| WO | WO-2012161683 | 11/2012 |

OTHER PUBLICATIONS

Dong, et al., "Minimally Invasive Surface-Enhanced Raman Scattering Detection with Depth Profiles Based on a Surface-Enhanced Raman Scattering-Active Acupuncture Needle" Analytical Chemistry. vol. 83, No. 16, Aug. 15, 2011, pp. 6191-6195.

International Search Report and Written Opinion dated Oct. 16, 2013,issued on PCT Patent Application No. PCT/US2013/023660 dated Jan. 29, 2013, Korean Intellectual Property Office.

Ling, Y. et al., Implantable Magnetic Relaxation Sensors Measure Cumulative Exposure to Cardiac Biomarkers, (Web Page), Feb. 13, 2011, pp. 273-277. http://www.nature.com/nbt/journal/v29/n3/full/nbt.1780.html.

Dong, Jian, et al. "Glucose-Responsive Multifunctional Acupuncture Needle: A universal SERS detection strategy of small biomolecules in vivo." Analytical Methods 4.11 (2012): 3879-3883.

* cited by examiner

APPARATUS HAVING SURFACE-ENHANCED SPECTROSCOPY ELEMENTS ON AN EXTERIOR SURFACE

CLAIM FOR PRIORITY

The present application is a national stage filing under 35 U.S.C 371 of PCT application number PCT/US2013/023660, having an international filing date of Jan. 29, 2013, the disclosure of which is hereby incorporated by reference in its entirety.

BACKGROUND

In surface-enhanced spectroscopy (SES), such as surface-enhanced Raman spectroscopy (SERS), vibrationally excitable levels of an analyte are probed. The energy of a photon can shift by an amount equal to that of the vibrational level excited by the photon (Raman scattering). A Raman spectrum, which consists of a wavelength distribution of bands corresponding to molecular vibrations specific to the analyte being probed, may be detected to identify the analyte. In SERS, the analyte molecules are in contact or close proximity, for instance, less than tens of nanometers, to metal nano-particles that may be or may not be coated with a dielectric, such as silicon dioxide, silicon nitride, and a polymer, that, once excited by light, support plasmon modes (collective oscillations of free electron density, which create strong near fields around the metal nano-particles. These fields can couple to analyte molecules in the near field regions enhancing the emission of scattered signals from the analyte molecules.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1A:
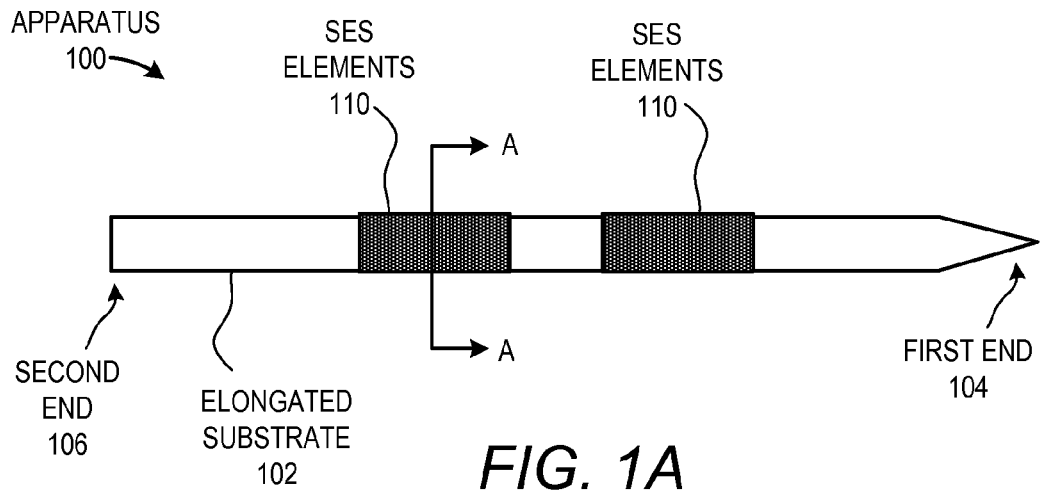
FIG. 1A shows a simplified side view of an apparatus for performing spectroscopy, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on. In addition, the term "light" refers to electromagnetic radiation with wavelengths in the visible and non-visible portions of the electromagnetic spectrum, including infrared, near infrared, and ultra-violet portions of the electromagnetic spectrum.

Disclosed herein are apparatuses for performing spectroscopy, systems for performing surface-enhanced spectroscopy (SES), methods for fabricating an apparatus, and methods for performing spectroscopy using the apparatus. The apparatus disclosed herein may include an elongated substrate having a shape and size to be inserted into a specimen, in which the elongated substrate has a first end and a second end. The apparatuses may also include a plurality of SES elements positioned on an exterior surface of the elongated substrate at a location between the first end and the second end of the elongated substrate. According to an example, the apparatuses may also include a cover layer to protect the SES elements during insertion and/or implantation of the apparatus into a specimen. The cover layer may be selectively removable and/or include a porous membrane that substantially prevents certain particles from contacting the plurality of SES elements.

According to an example, the elongated substrate on which the SES elements may be provided may be an acupuncture needle, in which the SES elements are provided near the insertion tip of the acupuncture needle. In one regard, the SES elements may be positioned at desired locations of a specimen in a relatively simple manner. That is, conventional techniques associated with inserting acupuncture needles may be employed to insert the apparatus disclosed herein to position the SES elements in a desired fluid location of the specimen.

In addition, the SES elements may be provided around the external circumference of the elongated substrate. As such, at least some of the SES elements may receive an illumination beam (excitation light) regardless of the rotational orientation in which the elongated substrate is inserted into a specimen. In one regard, for instance, if the apparatus rotates about its central longitudinal axis, the apparatus may still be used for performing spectroscopy.

By way of example, the apparatuses disclosed herein may be implemented in the medical management of health and disease. For instance, the apparatuses disclosed herein may be used to perform relatively fast and accurate profiling (analytics) and discovery of biomarkers from physiological analytes as well as physiological states that are critical for early diagnosis, disease prevention, screening, monitoring, diagnosis, treatments, and wellness improvements, especially evaluation and assessment of medical procedures and treatments. As discussed herein, the apparatuses may be used to perform spectroscopy in real-time (online) and/or offline to direct and collect identification of single or multiple states and metrics, and distributions of specific biomarkers and native or artificially introduced reporter molecules, and discovery of a new or a collective profile of potential biomarkers.

With reference first to FIG. 1A, there is shown a simplified side view of an apparatus 100 for performing spectroscopy, according to an example. It should be understood that the apparatus 100 depicted in FIG. 1A may include additional components and that some of the components described herein may be removed and/or modified without departing from a scope of the apparatus 100. It should also be understood that the components depicted in FIG. 1A are not drawn to scale and thus, the components may have different relative sizes with respect to each other than as shown therein.

Generally speaking, the apparatus 100 may be implemented to perform spectroscopy, which may include surface-enhanced Raman spectroscopy (SERS), surface-enhanced luminescence detection, surface-enhanced fluorescence detection, or other types of surface-enhanced optically enhanced detection. In this regard, the apparatus 100 may include an elongated substrate 102 and a plurality of surface-enhanced spectroscopy (SES) elements 110. The SES elements 110 have been depicted as extending at a distance above the surface of the elongated substrate 102. However, as discussed in greater detail below, the SES elements 110 may be relatively small elements, for instance, having nano-scale dimensions, and thus, it should be understood that in some examples, the SES elements 110 may not be as visible as they are shown in FIG. 1A. As such, it should be clearly understood that the depiction of the SES elements 110 in FIG. 1A as well as in the other figures are for purposes of simplified illustration and description.

The elongated substrate 102 may extend along a lateral axis and may have a first end 104 and a second end 106. Each of the SES elements 110 may be provided in respective groups at multiple locations along the elongated substrate 102 between the first end 104 and the second end 106. The SES elements 110 depicted in FIG. 1A may therefore represent respective groups of SES elements 110 as discussed in greater detail below.

The apparatus 100 may have a size, a configuration, and may be fabricated of materials that make the apparatus 100 suitable for insertion and/or implantation into a specimen. The first end 104 may also have a pointed tip, which generally enables the apparatus 100 to be inserted through a skin layer of a specimen. The pointed tip, may however, be omitted and the apparatus 100 may be inserted by way of a conventional cylindrical acupuncture insertion device. By way of particular example, the elongated substrate 102 of the apparatus 100 may be an acupuncture needle and may thus to be inserted into the specimen in manners similar to those employed to insert acupuncture needles into humans. The second end 106 of the elongated substrate 102 may include a handle (not shown) to facilitate insertion of the apparatus 100, or at least a portion of the apparatus 102, into the specimen.

According to an example, the apparatus 100 may be implemented to perform spectroscopy in vivo, i.e., following insertion and/or implantation of the apparatus 100 into a specimen, such as a human, an animal, an insect, a plant, non-living item, etc. The apparatus 100 may thus be implemented to analyze particles, such as molecules, in a fluid specimen, such as blood, lymph, saliva, interstitial fluid, etc. The apparatus 100 may alternatively be implemented in spectroscopy applications that do not involve implantation of the apparatus 100.

The elongated substrate 102 may thus include any material suitable for insertion and/or implantation into a specimen, such as silicon, polymer, plastic, silver, titanium, etc. In other examples, in which the apparatus 100 is to be implemented without being inserted and/or implanted into a specimen, the elongated substrate 102 may also include other materials, such as materials that may be toxic to a specimen. According to an example, the elongated substrate 102 may have a diameter (or width) that is anywhere between about 0.1 mm to about 10 mm and a length that is anywhere between about 1 mm to about 100 mm. In addition, the SES elements 110 may be arranged in groups that span over relatively small sections of the elongated substrate 102. By way of example, each of groups of SES elements 110 may have widths that are anywhere between about 5 microns to about 500 microns.

The SES elements 110 may be provided on any surface of the elongated substrate 102. Particularly, the SES elements 110 may be arranged on the elongated substrate 102 in different groupings. That is, one group of SES elements 110 may be positioned at one location on the elongated substrate 102 and another group of SES elements 110 may be positioned at a second location on the elongated substrate 102. It should however be understood that the depiction of the apparatus 100 is for purposes of illustration and that various modifications to the components of the apparatus 100 may be made without departing from a scope of the apparatus 100. For instance, the plurality of SES elements 110 may be arranged to include alternate configurations. By way of example, a single group of SES elements 110 may be positioned along the surface of the elongated substrate 102. As another example, additional groups of SES elements 110 may be positioned along substantially the entire length of the elongated substrate 102.

Generally speaking, the SES elements 110 may be elements that enhance the emission of any of light, fluorescence, luminescence, etc., by particles in contact with and/or in relatively close proximities to the SES elements 110 and therefore enhance sensing operations, such as surface enhanced Raman spectroscopy (SERS), enhanced photoluminescence, enhanced fluorescence, etc., on the particles. The SES elements 110 may include plasmonic nanoparticles or nanostructures, which may include plasmon-supporting materials such as but not limited to, gold (Au), silver (Ag), and copper (Cu). The SES elements 110 may also include structures arranged in various ordered or random configurations on substrates.

The SES 110 elements may have nanoscale surface roughness, which is generally characterized by nanoscale surface features on the surface of the layer(s) and may be produced spontaneously during deposition of the plasmon-supporting material layer(s). By definition herein, a plasmon-supporting material may be a material that facilitates scattering of signals and the production or emission of a signal from an analyte on or near the material during spectroscopy.

In some examples, the SES elements 110 may be functionalized to facilitate adsorption of analyte molecules. For example, surfaces of the SES elements 110 may be functionalized such that a particular class of analytes is attracted and may bond or be preferentially adsorbed onto the SES elements 110. Various manners in which the SES elements 110 may enhance scattered light emissions from analyte molecules are described in greater detail herein below.

The apparatus 100 may include a relatively large number of SES elements 110 to substantially increase the enhancement of signal emissions (e.g., Raman scattered light, luminescence, fluorescence, etc.) from an analyte. In addition, the plurality of SES elements 110 may include any suitable dimensions that are sufficient for the SES elements 110 to substantially enhance the signal emissions and for a detector to detect the emitted signals.

Figure 1B:
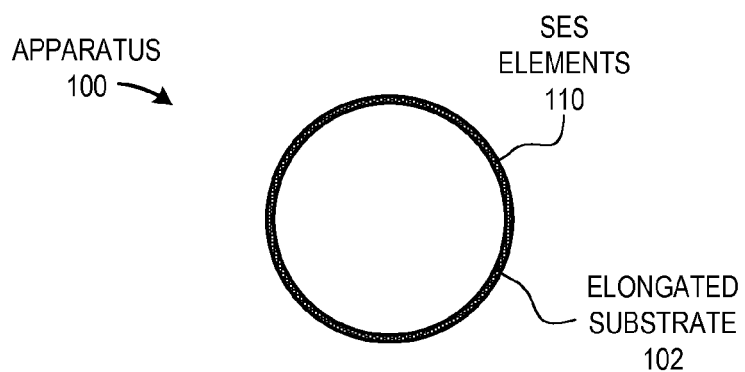
FIG. 1B shows an enlarged, cross-sectional view of the apparatus depicted in FIG. 1A taken along lines A-A, according to an example of the present disclosure.

Turning now to FIG. 1B, there is shown a simplified cross-sectional side view of the apparatus 100 taken along lines A-A in FIG. 1A, according to an example. The elongated substrate 102 may have a circular cross section and the SES elements 110 may extend around the circumference of the elongated substrate 102. In addition, this arrangement of the SES elements 110 around the circumference of the elongated structure 102 may substantially enhance the likelihood that light will be directed onto a group of SES elements 110 regardless of the rotational orientation of the elongated substrate 102 along the longitudinal axis of the elongated substrate 102.

It should be understood that the apparatus 100 depicted in FIG. 1B may be modified in various respects without departing from a scope of the apparatus 100. For instance, instead of spanning over the entire circumference of the elongated substrate 102, the SES elements 110 may be provided on a portion of the circumference of the elongated substrate 102. By way of example, the SES elements 110 may be provided on one half of the elongated substrate 102 circumference. As another example, the SES elements 110 may be arranged in multiple groups around the circumference of the elongated substrate 102. In this example, gaps may be provided between respective groups of the SES elements 110 along the circumference of the elongated substrate 102.

Figure 1C:
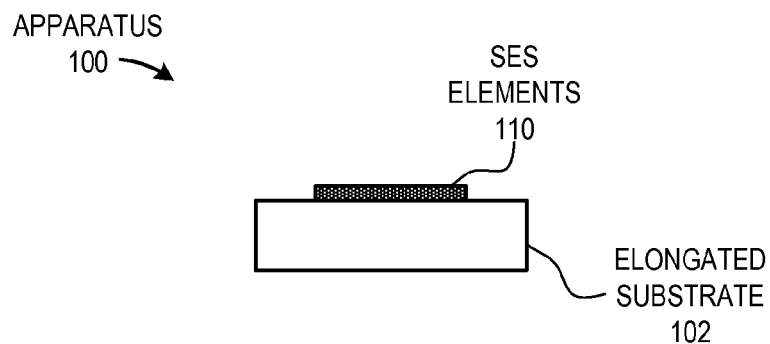
FIG. 1C shows a simplified cross-sectional view of the apparatus depicted in FIG. 1A, according to another example of the present disclosure.

Turning now to FIG. 1C, there is shown a simplified cross-sectional side view of the apparatus 100, according to another example. In the example depicted in FIG. 1C, the elongated substrate 102 is depicted as having a rectangular cross section and the SES elements 110 are depicted as being arranged on one surface of the elongated substrate. It should be understood that the elongated substrate 102 may have other cross-sectional shapes without departing from a scope of the apparatus 100. For instance, the elongated substrate 102 may have other polygon shapes, an oval shape, etc. Moreover, although the elongated substrate 102 has been depicted as having a solid structure, the elongated substrate 102 may instead have a fully or partially hollow structure. In addition, or alternatively, the SES elements 110 may be provided along multiple sides of the elongated substrate 102.

Figure 2A:
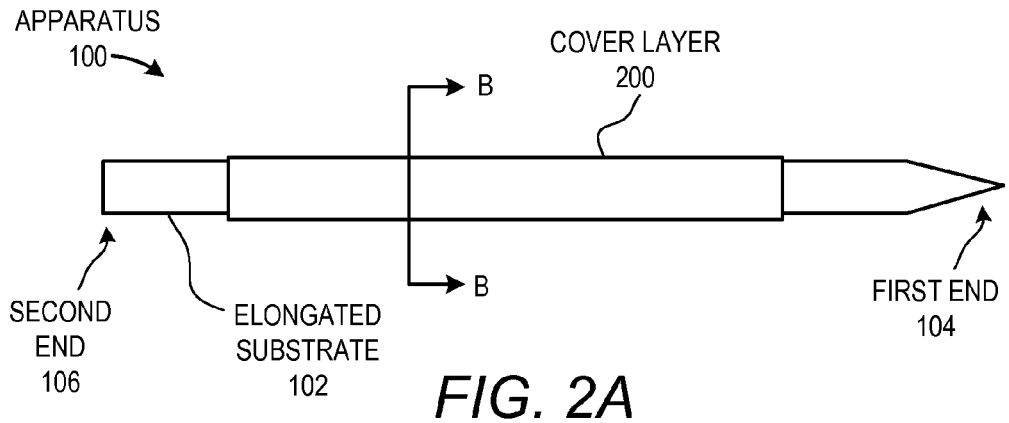
FIGS. 2A-2C, respectively show diagrams of an apparatus for performing spectroscopy, according to another example of the present disclosure.

Turning now to FIG. 2A, there is shown a simplified side view of the apparatus 100 for performing spectroscopy depicted in FIG. 1A, according to another example. The apparatus 100 depicted in FIG. 2A may include all of the same components as those contained in the apparatus 100 depicted in FIG. 1A and thus, those components will not be described in greater detail with respect to the apparatus 100 depicted in FIG. 2A.

Figure 2B:
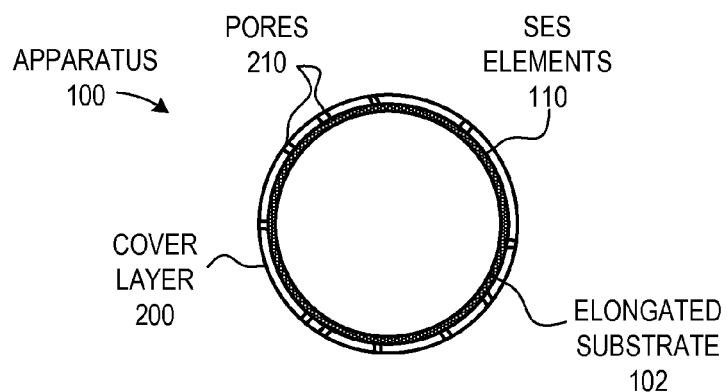

As shown in FIG. 2A, the apparatus 100 may include a cover layer 200 that extends over the SES elements 110. As shown in FIG. 2B, which is a cross-sectional side view of the apparatus 100 taken along lines B-B in FIG. 2A, the cover layer 200 may also extend around the circumference of the elongated substrate 102. The apparatus 100 in FIG. 2B has also been depicted as including optional pores 210, which are described in greater detail below. According to an example, the cover layer 200 may be a protective layer that is to protect the SES elements 110 during insertion of the apparatus 100 into a specimen. In addition, or alternatively, the cover layer 200 may protect the SES elements 110 following implantation of the apparatus 110 into a specimen. In any regard, the cover layer 200 may be formed of any suitable material for protecting the SES elements 110. For instance, the cover layer 200 may be formed of a biodegradable material that is non-toxic to humans, a combination of biocompatible materials, including synthetic and biological polymer materials, metals, lipids, carbohydrates, etc.

According to a particular example, the cover layer 200 may be formed of a material that is to dissolve after being inserted into the specimen. In this example, the cover layer 200 may be formed of a material and of a particular size that enables the cover layer 200 to dissolve after being exposed to a fluid in the specimen following a predetermined length of time. According to another example, the cover layer 200 may be formed of a material that is to be removed when an external stimulus is applied onto the cover layer 200. In this example, the external stimulus may include, for instance, light, heat, chemical agents, biological agents, etc. Thus, for instance, an external stimulus may be applied onto the cover layer 200 following insertion and/or implantation of the apparatus 100 into the specimen. In one regard, therefore, the cover layer 200 may protect the SES elements 110 during insertion and/or implantation into the specimen and may be removed after insertion and/or implantation to expose the SES elements 110.

According to another example, the cover layer 200 may include a drug that is to be delivered into the specimen. In this example, the cover layer 200 may, in addition or alternatively, be provided over areas of the substrate 102 on which the SES elements 110 have not been provided. As a further example, the cover layer 200 may cover a drug material such that the drug may be delivered into the specimen when the cover layer 200 is removed. Thus, for instance, the cover layer 200 in these examples may be removed following performance of a spectroscopy operation that indicates that the drug is to be delivered into the specimen.

According to a further example, the cover layer 200 may include a porous membrane having a plurality of pores 210 (FIG. 2B). The cover layer 200 in this example may substantially block various materials from contacting the SES elements 110 beneath the cover layer 200. Only particles having a sufficiently small size to fit through the pores 210 of the cover layer 200 may thus be able to contact the SES elements 110. In one regard, the cover layer 200 may substantially prevent larger unwanted particles from blocking or damaging the SES elements 110. The pores 210 may also have particular shapes to enable selective passage of molecules having particular shapes. In addition, or alternatively, the cover layer 200 may be functionalized with receptors of molecules that are not expected to pass through the pores 210. In this example, the cover layer 200 may be functionalized with receptors of various types of molecules so that multiple species in the fluid may be selectively and efficiently blocked.

The cover layer 200 may also be formed to enable light, including excitation light and scattered signals, to substantially pass therethrough. In this example, the cover layer 200 may be formed to have a sufficiently thin size and/or formed of an optically transparent material to enable the light and signals to pass therethrough. By way of particular example, the cover layer 200 may have a thickness that is between about 2 nm to about 500 nm. Additionally, although the cover layer 200 has been depicted as having a relatively thin configuration, the cover layer 200 may alternatively have a thicker, sponge-like, or scaffold-like matrix configuration.

The cover layer 200 in this example may be composed of any suitable material that enables the cover layer 200 to perform the functions in the apparatus 100 discussed herein. Examples of suitable materials for the cover layer 200 may include cellulose acetate, urethane based polymer (for example, polyurethane, polyether urethane, or polycarbonate urethane), ethylene glycol based polymer, heparin-functionalized polymer, a combination of these materials, etc.

By way of example, the pores 210 may be fabricated into the cover layer 200 through implementation of a molecular imprinting technique. In this technique, for instance, molecules that are to be allowed to pass through the cover layer 200 may be mixed with a polymer material and the mixture may be formed into a relatively thin sheet and resist cured, e.g., UV cured. The molecule may then be dissolved from the relatively thin sheet of mixed material, thereby leaving pores 210 that are specially shaped to the molecules that are to be allowed to pass through the cover layer 200. The thin sheet of material may then be positioned on a supporting porous sub-layer (not shown) and the combined layers may be positioned over the SES elements 110.

According to another example, the cover layer 200 includes a lipid bilayer, which may be a thin polar membrane made of two layers of lipid or phospholipid molecules. The lipid bilayer may include relatively flat sheets of lipid molecules that form a continuous barrier around cells. The lipid bilayer may include proteins or channels that serve as transporting vehicles through the lipid bilayer membrane. In this regard, the proteins may selectively transport molecules, for instance, molecules having sufficiently small sizes to pass through the lipid bilayer membrane, through the lipid bilayer membrane, which may therefore enable the lipid bilayer membrane to operate as a filter. The lipid bilayer may be collected from naturally occurring cells and/or fabricated synthetically from lipid molecules. In any regard, the lipid bilayer may be positioned, for instance, by coating the lipid bilayer on a supporting porous sub-layer (not shown) and the combined layers may be positioned over the SES elements 110.

According to a further example, the cover layer 200 may be functionalized to include host molecules, such as crown ethers, cyclodextrins, etc., that are to bond to corresponding guest molecules. Because the molecules corresponding to the host molecules may bond to the host molecules, the corresponding guest molecules may substantially be prevented from passing through the cover layer 200 and contacting the SES elements 110.

Figure 2C:
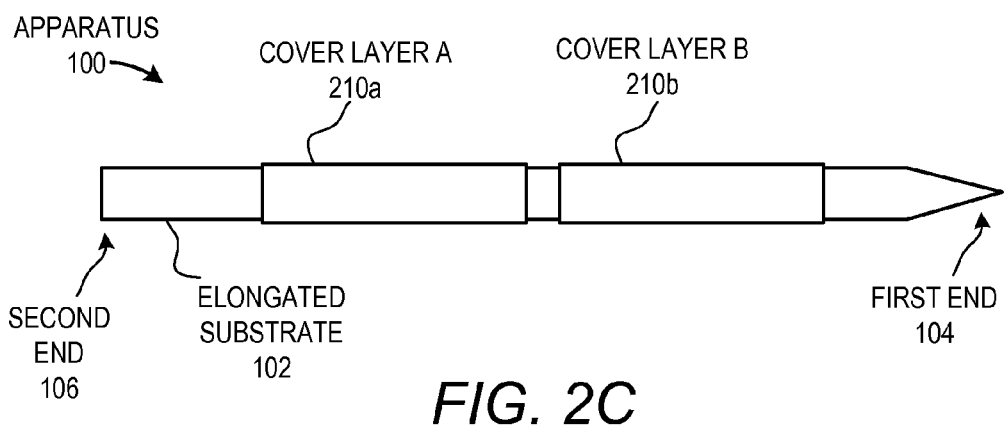

Turning now to FIG. 2C, there is shown a simplified side view of the apparatus 100 for performing spectroscopy depicted in FIG. 2A, according to another example. The apparatus 100 shown in FIG. 2C may differ from the apparatus 100 depicted in FIG. 2A, in that, the apparatus 100 may include a plurality of cover layers 210a and 210b. Particularly, each of the cover layers 210a and 210b may cover areas over respective sets of SES elements 110.

According to an example, each of the cover layers 210a and 210b may be formed of materials and/or may have different configurations, for instance, thicknesses, that may cause the cover layers 210a and 210b to dissolve at different rates after exposure to a fluid in the specimen or to be photolyzed by light. In this example, different sets of SES elements 110 may be exposed to the fluid in the specimen at different times or to the light for photolysis.

In another example, the cover layers 210a and 210b may be formed of the same materials and may have the same configurations. In this example, an external stimulus may be applied to the cover layers 210a and 210b at different times to expose the different sets of SES elements 110 contained beneath the cover layers 210a and 210b. By selectively exposing different groups of the SES elements 110 at different times, the apparatus 100 may be used to detect changes in condition of the specimen over time.

As shown in FIGS. 2A-2C, the cover layers 200, 210a, 210b may extend at a distance above the surface of the elongated substrate 102. However, the cover layers 200, 210a, 210b may include relatively thin layers to therefore enable the apparatus 100 to be inserted into a specimen without substantial interference from the cover layers 200, 210a, 210b. It should be understood that in some examples, the cover layers 200, 210a, 210b may not be as visible as they are shown in FIGS. 2A-2C. As such, it should be clearly understood that the depiction of the cover layers 200, 210a, 210b in FIGS. 2A-2C is for purposes of simplified illustration and description.

Figure 3:
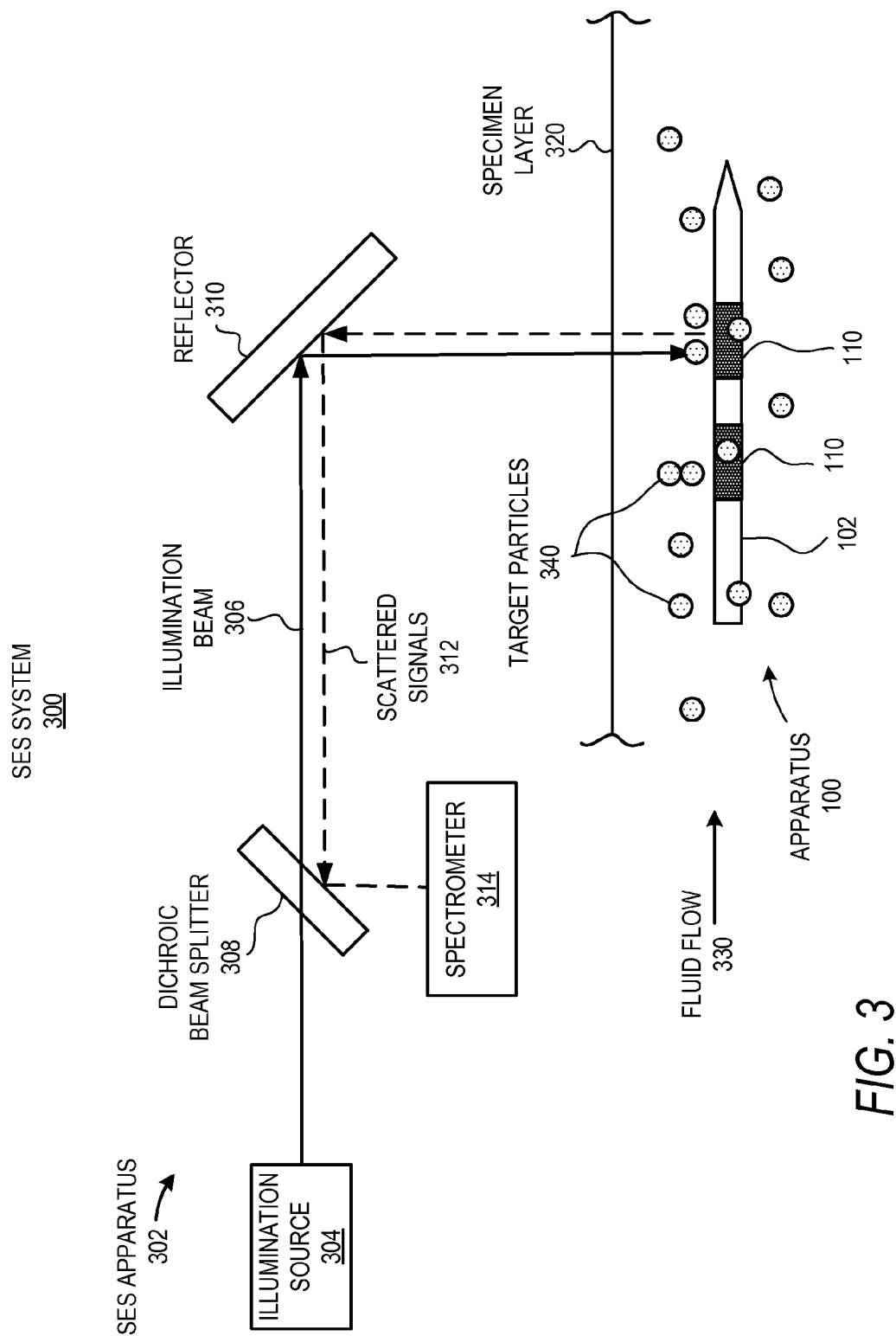
FIG. 3 shows a diagram of a SES system that may include a SES apparatus and an apparatus for performing spectroscopy, according to an example of the present disclosure.

Turning now to FIG. 3, there is shown a diagram of a SES system 300 that includes a SES apparatus 302 and an apparatus 100 for performing SES, according to an example. It should be understood that the SES system 300 depicted in FIG. 3 may include additional components and that some of the components described herein may be removed and/or modified without departing from a scope of the SES system 300. It should also be understood that the components depicted in FIG. 3 are not drawn to scale and thus, the components may have different relative sizes with respect to each other than as shown therein.

The SES apparatus 302 may include an illumination source 304, a dichroic beam splitter 308, a reflector 310, and a spectrometer 314. The illumination source 304 may emit a beam of illumination 306 (such as a laser beam, an LED beam, or other type of light beam) through the dichroic beam splitter 308. The illumination beam 306 may also be reflected by the reflector 310 onto the apparatus 100. The illumination beam 306 may penetrate through a specimen layer 320 to illuminate the SES elements 110 and target particles 340 in relatively close proximities to and/or contacting the SES elements 110.

In FIG. 3, the target particles 340 are depicted as being contained in a fluid flow 330, which may include, for instance, blood, lymph, saliva, interstitial fluid, etc. The target particles 340 may include, for instance, native and/or artificially introduced reporter molecules, biomarkers, etc. Generally speaking, the biomarkers and reporter molecules may be derived from blood and other body fluids as well as molecular indicators of the conformations and chemical/physical states of the medical parameters for both wellness and ailments. The fluid flow 330 may include the target particles 340 and other bodily fluids. As the fluid 330 flows by the apparatus 100, some of the target particles 340 may contact, and in some instances, bind with some of the SES elements 110.

Generally speaking, the illumination beam 306 may operate as an excitation light on the SES elements 110, which may cause near fields around the SES elements 110 to be created. The near fields around the SES elements 110 may couple to the target particles 340 in the vicinities of the SES elements 110. The metallic nanoparticles (or other plasmonic structures) of the SES elements 110 may also act to enhance the signal emission process of the target particles 340. As a result, scattered signals 312 (e.g., Raman scattered light, luminescence, fluorescence, etc.) may be emitted from the target particles 340 and the emission of the scattered signals 312 may be enhanced by the SES elements 110. A portion of the scattered signals 312, which may be emitted in all directions from the target particles 340 near the SES elements 110, may be emitted toward the reflector 310.

The apparatus 100 has been depicted as being inserted and/or implanted underneath a layer 320 of a specimen, which may include, for instance, a skin layer, body tissue, vein walls blood vessels, lymph ducts, a cover, etc., under which the apparatus 100 may be inserted and/or implanted. In another example, the illumination beam 306 may pass through a gaseous or liquid environment in which the apparatus 100 may have been positioned. In any regard, the scattered signals 312 may also pass through the surface layer and/or the gaseous or liquid environment.

The scattered signals 312 may be reflected from the reflector 310 and directed back to the dichroic beam splitter 308. The dichroic beam splitter 308 may also reflect the scattered signals 312 toward the spectrometer 314. The spectrometer 314 may include optical elements, such as, slits, gratings, lenses, etc., that allow for the separation and measurement of different wavelengths of light. The spectrometer 314 may also include a detector, e.g., a photomultiplier tube (PMT), a charge-coupled device (CCD), a complementary metal-oxide-semiconductor (CMOS), etc., detector) to measure the intensities of the separated wavelength bands. The measured intensities of the separated wavelength bands may be used to identify the analyte.

Various modifications may be made to the SES apparatus 302 depicted in FIG. 3 without departing from a scope of the SES system 300. For instance, the reflector 310 may have a parabolic shape that is to focus the illumination beam 306 onto the SES elements 110 and/or to focus the scattered signals 312 onto the dichroic beam splitter 308. As a yet further example, various additional optical components, e.g., mirrors, prisms, optical fibers, etc., may be positioned to direct the illumination beam 306 on the SES elements 110 and/or the scattered signals 312 to the spectrometer 314.

Figure 4A:
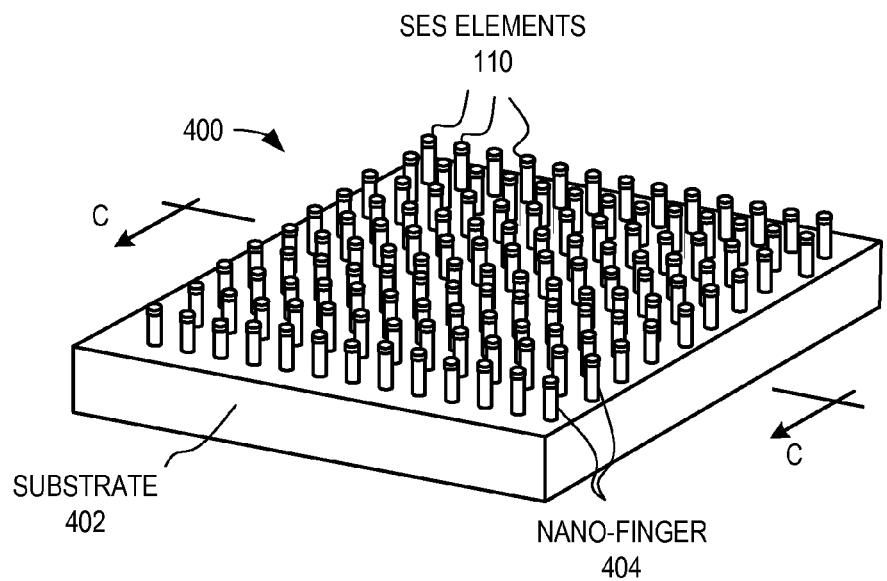
FIG. 4A shows an isometric view of an array of SES elements, in this instance nano-fingers, that may be implemented in the apparatus depicted in FIGS. 1A-3, according to an example of the present disclosure.
Figure 4B:
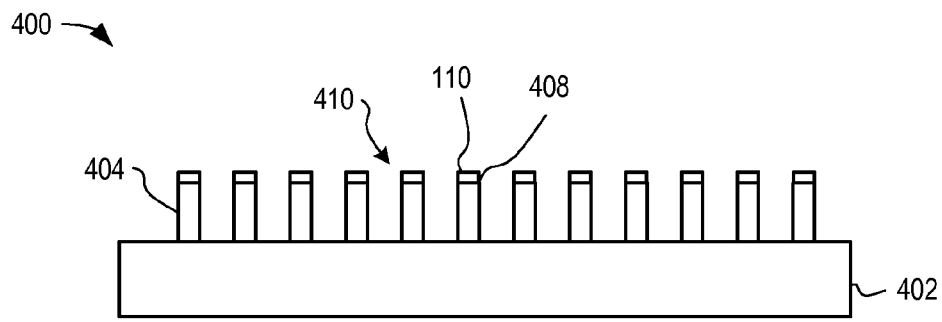
FIGS. 4B and 4C, respectively show cross-sectional views along a line C-C, shown in FIG. 4A, prior to and following collapse of the nano-fingers, according to examples of the present disclosure.
Figure 4C:
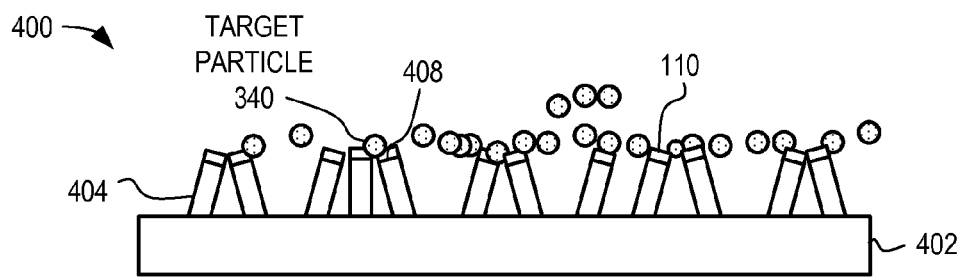

Turning now to FIGS. 4A-4C, there are respectively shown an isometric view and side views of an array 400 of SES elements 110, according to an example. It should be understood that the array 400 depicted in FIGS. 4A-4C may include additional components and that some of the components described herein may be removed and/or modified without departing from a scope of the apparatus 100 disclosed herein. It should also be understood that the components depicted in FIGS. 4A-4C are not drawn to scale and thus, the components may have different relative sizes with respect to each than as shown therein.

Generally speaking, the array 400 of SES elements 110 depicted in FIGS. 4A-4C is an example of a plurality of SES elements 110 depicted in FIGS. 1A-3. Particularly, in the array 400, the SES elements 110 may be positioned on the tops of respective nano-fingers 404 that extend above a surface of a substrate 402. The substrate 402 may be formed of any suitable material, such as, silicon, silicon nitride, glass, plastic, polymer, $SiO_2$, $Al_2O_3$, aluminum, etc., or a combination of these materials, etc. The substrate 402 may be the elongated substrate 102 depicted in FIG. 1A or the substrate 402 may be a separate substrate that may be positioned on top of the elongated substrate 102.

According to an example, the nano-fingers 404 may have dimensions that are in the nanometer range, for instance, dimensions that may be less than about 500 nm, and may be formed of a relatively flexible material to enable the nano-fingers 404 to be laterally bendable or collapsible, for instance, to enable tips of the nano-fingers 404 to move toward each other, as discussed in greater detail herein below. Examples of suitable materials for the nano-fingers 404 may include polymer materials, such as, UV-curable or thermal curable imprinting resist, polyalkylacrylate, polysiloxane, polydimethylsiloxane (PDMS) elastomer, polyimide, polyethylene, polypropelene, polyurethane, fluoropolymer, etc., or any combination thereof, metallic materials, such as, gold, silver, aluminum, etc., semiconductor materials, etc., and combinations thereof.

The nano-fingers 404 may be attached to the surface of the substrate 402 through any suitable attachment mechanism. For instance, the nano-fingers 404 may be grown directly on the substrate 402 surface through use of various suitable nano-structure growing techniques. As another example, the nano-fingers 404 may be integrally formed with the substrate 402. In this example, for instance, a portion of the material from which the substrate 402 may be fabricated may be etched or otherwise processed to form the nano-fingers 404. In a further example, a separate layer of material may be adhered to the substrate 402 surface and the separate layer of material may be etched or otherwise processed to form the nano-fingers 404. In various examples, the nano-fingers 404 may be fabricated through a nanoimprinting or an embossing process in which a template of relatively rigid pillars may be employed in a multi-step imprinting process on a polymer matrix to form the nano-fingers 404. In these examples, a template may be formed through photolithography or other advanced lithography with the desired patterning to arrange the nano-fingers 404 in the predetermined arrangement. More particularly, for instance, the desired patterns may be designed on a mold by any of E-beam lithography, photolithography, laser interference lithography, Focused Ion Beam (FIB), self-assembly of spheres, etc. In addition, the pattern may be transferred onto another substrate, for instance, a silicon, glass, or polymer substrate (PDMS, polyimide, polycarbonate, etc.). Various other processes, such as, etching, and various techniques used in the fabrication of micro-electromechanical systems (MEMS) and nano-electromechanical systems (NEMS) may also be used to fabricate the nano-fingers 404.

The nano-fingers 404 have been depicted as having substantially cylindrical cross-sections. It should, however, be understood that the nano-fingers 404 may have other shaped cross-sections, such as, for instance, rectangular, square, triangular, etc. In addition, or alternatively, the nano-fingers 404 may be formed with features, such as, notches, bulges, etc., to substantially cause the nano-fingers 404 to be inclined to collapse in particular directions. Thus, for instance, two or more adjacent nano-fingers 404 may include the features to increase the likelihood that the nano-fingers 404 collapse toward each other. Various manners in which the nano-fingers 404 may be collapsed are described in greater detail herein below.

The array 400 may include a substantially random distribution of nano-fingers 404 or a predetermined configuration of nano-fingers 404. In any regard, according to an example, the nano-fingers 404 may be arranged with respect to each other such that the tips of at least two neighboring nano-fingers 404 are able to be brought into close proximity with each other when the nano-fingers 404 are in a partially collapsed state. By way of particular example, the neighboring nano-fingers 404 may be positioned less than about 100 nanometers apart from each other. According to a particular example, the nano-fingers 404 may be patterned on the substrate 402 such that neighboring ones of the nano-fingers 404 preferentially collapse into predefined geometries, for instance, triangles, squares, pentagons, etc.

Turning now to FIG. 4B, there is shown a cross-sectional view along a line C-C, shown in FIG. 4A, of the array 400, in accordance with an example. As shown therein, each of the tips 408 of the nano-fingers 404 may include a respective SES element 110 disposed thereon. The SES elements 110, which may include metallic nanoparticles, may be deposited onto the tips 408 of the nano-fingers 404 through one of, for instance, physical vapor deposition (PVD), chemical vapor deposition (CVD), sputtering, etc., of metallic material, or self-assembly of pre-synthesized nano-particles.

Although the nano-fingers 404 have been depicted in FIGS. 4A-4B as each extending vertically and at the same heights with respect to each other, it should be understood that some of the nano-fingers 404 may extend at various angles and heights with respect to each other. The differences in angles and/or heights between the nano-fingers 404 may occur, for instance, due to differences arising from manufacturing or growth variances existent in the fabrication of the nano-fingers 404 and the deposition of the SES elements 104 on the nano-fingers 404, etc.

As shown in FIG. 4B, the nano-fingers 404 may be in a first position, in which the tips 408 may be in a substantially spaced arrangement with respect to each other. The gaps 410 between the tips 408 may be of sufficiently large size to enable a liquid to be positioned in the gaps 410. In addition, the gaps 410 may be of sufficiently small size to enable the tips 408 of at least some of the nano-fingers 404 to be drawn toward each other as the liquid provided in the gaps 410 evaporates, through, for instance, capillary forces applied on the tips 408 as the liquid evaporates.

Turning now to FIG. 4C, there is shown a cross-sectional view along a line C-C, shown in FIG. 4A, of the array 400, following evaporation of the liquid, according to an example. The view depicted in FIG. 4C may be identical to the view depicted in FIG. 4B, except that the nano-fingers 404 may be in a second position, in which the tips 408 of some of the nano-fingers 404 have been drawn toward with each other. According to an example, the tips 408 of some of the nano-fingers 404 may be in and may remain in relatively close proximity to each other for a period of time due to the capillary forces applied on adjacent ones of the nano-fingers 404 during and following evaporation of the liquid (not shown) in the gaps 410 between the tips 408. In addition, the SES elements 110 on the adjacent tips 408 may bond to each other through, for instance, gold-gold bonding, a binding molecule (not shown), etc.

In one regard, the tips 408 of the nano-fingers 404 may be caused to be drawn toward each other as shown in FIG. 4C to enhance signal emission by the target particles 340 in the near fields of the SES elements 110 because the relatively small gaps (or no gaps) between the SES elements 110 on the adjacent tips 408 create "hot spots" having relatively large electric field strengths. According to an example, the nano-fingers 404 may be positioned into the partially collapsed state depicted in FIG. 4C prior to introduction of a fluid flow 330 (FIG. 3) containing the target particles 340. According to another example, the nano-fingers 404 may be positioned into the partially collapsed state depicted in FIG. 4C prior to formation of the cover layer 200, 210a, 210b over the SES elements 110 depicted in FIGS. 2A-2C.

According to a further example, the SES elements 110 may be deposited and/or formed directly on the substrate 402. In addition, or alternatively, the SES elements 110 may initially be formed and positioned, for instance, as shown in FIG. 4C, such that the SES elements 110 are either touching each other or are in relatively close proximities to each other and the SES elements 110 may be transferred to another substrate, for instance, the elongated substrate 102.

Figure 5:
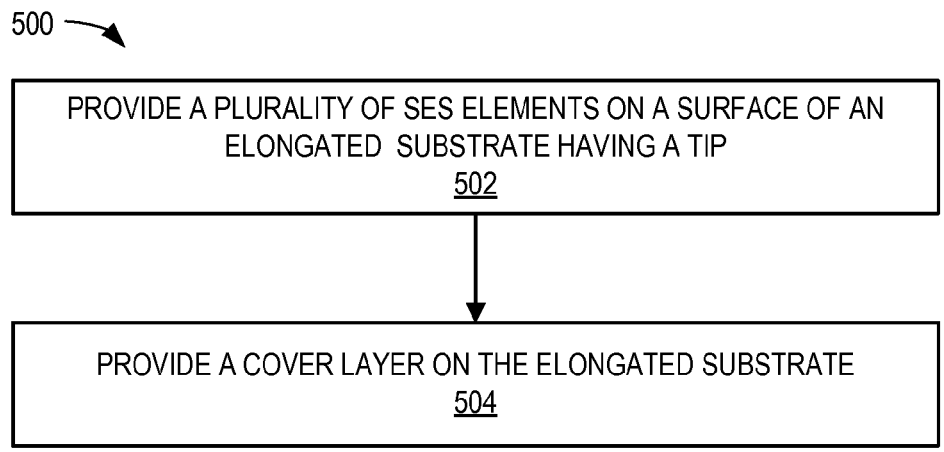
FIG. 5 shows a flow diagram of a method for fabricating an apparatus for performing spectroscopy, according to an example of the present disclosure.

Turning now to FIG. 5, there is shown a flow diagram of a method 500 for fabricating an apparatus 100 for performing spectroscopy, according to an example. It should be understood that the method 500 depicted in FIG. 5 may include additional processes and that some of the processes described herein may be removed and/or modified without departing from a scope of the method 500. In addition, although particular reference is made herein to the apparatus 100 as being fabricated through implementation of the method 500, it should be understood that the method 500 may be implemented to fabricate a differently configured apparatus without departing from a scope of the method 500.

At block 502, a plurality of SES elements 110 may be provided on a surface of an elongated substrate 102 having a shape and size to be inserted into a specimen, in which the elongated substrate 102 has a first end 104 and a second end 106. The first end 104 may have a pointed tip. As discussed above, the SES elements 110 may be provided on the surface of the elongated substrate 102 in any of a variety of manners.

At block 504, a cover layer 200, 210a, 210b may be provided on the elongated substrate 102. According to an example, the cover layer 200, 210a, 210b may be provided over the SES elements 110 to protect the SES elements 110 during insertion and/or following implantation of the apparatus 100 into a specimen. In addition, or alternatively, the cover layer 200, 210a, 210b may include a drug that is to be delivered to the specimen.

Figure 6:
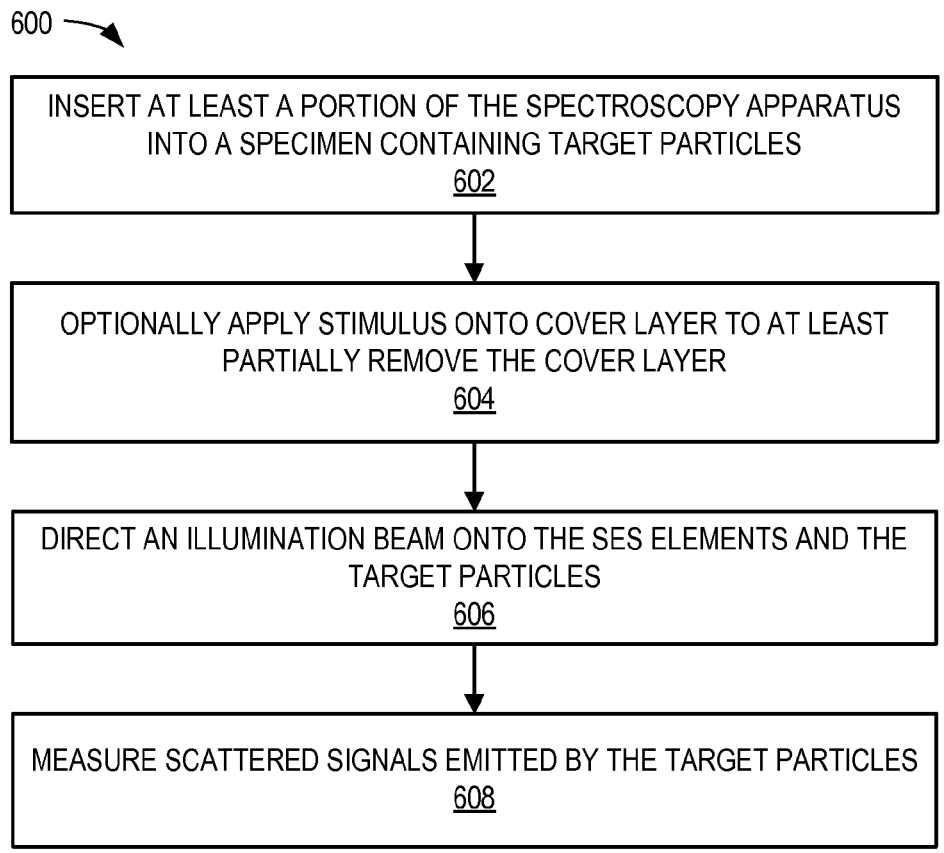
FIG. 6 shows a flow diagram of a method for using an apparatus for performing spectroscopy, according to an example of the present disclosure.

Turning now to FIG. 6, there is shown a flow diagram of a method 600 for using an apparatus 100 for performing spectroscopy, according to an example. It should be understood that the method 600 depicted in FIG. 6 may include additional processes and that some of the processes described herein may be removed and/or modified without departing from a scope of the method 600. In addition, although particular reference is made herein to the apparatus 100 as being used in the method 600, it should be understood that the method 600 may use a differently configured apparatus without departing from a scope of the method 600.

At block 602, at least a portion of the apparatus 100 may be inserted into a specimen that includes a fluid 330 containing target particles 340 to cause at least some of the target particles to contact the plurality of SES elements 110. According to an example in which the elongated substrate 102 of the apparatus 100 is an acupuncture needle, the apparatus 100 may be inserted into the specimen in manners similar to those employed to insert acupuncture needles into a specimen. For instance, the apparatus 100 may be inserted directly through an outer layer, e.g., skin, of the specimen without requiring use of a separate delivery mechanism.

At block 604, a stimulus may optionally be applied onto a cover layer 200, 210a, 210b to at least partially remove the cover layer 200, 210a, 210b. As discussed above, the stimulus may include any of heat, light, chemical agents, biological agents, etc. In addition, the application of the stimulus at block 604 may be optional, for instance, in cases where the cover layer 200, 210a, 210b is formed of materials and/or configurations to cause the cover layer 200, 210a, 210b to dissolve after being exposed to a fluid in the specimen or to be photolyzed by light. In other examples in which the cover layer 200, 210a, 210b is formed of a porous membrane, the cover layer 200, 210a, 210b may be maintained over the SES elements 110.

At block 606, an illumination beam may be directed onto the plurality of SES elements 110 and the target particles 340 to cause the target particles 340 to emit scattered signals 312. As discussed above, the SES elements 110 may generally enhance emission of the scattered signals 312 from the target particles 340 that are in contact with or in relatively close proximity to the SES elements 110. In addition, the scattered signals 312 may be directed to a spectrometer 314.

At block 608, the scattered signals 312 emitted by the target particles 340 may be measured. The scattered signals 312 may be measured by the spectrometer 314 as discussed above with respect to FIG. 3.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. An apparatus for performing spectroscopy comprising:
   an elongated substrate having a shape and size to be inserted into a specimen, wherein the elongated substrate has a first end and a second end, and wherein the elongated substrate has a diameter or width that is between about 0.1 mm to about 10 mm; and
   a plurality of surface-enhanced spectroscopy (SES) elements positioned on an exterior surface of the elongated substrate at a location between the first end and the second end of the elongated substrate.

2. The apparatus according to claim 1, wherein the elongated substrate comprises an acupuncture needle.

3. The apparatus according to claim 1, wherein the elongated substrate comprises a circular cross-section and wherein the plurality of SES elements are positioned around an outer circumference of the elongated substrate at the location between the first end and the second end of the elongated substrate.

4. The apparatus according to claim 1, further comprising:
   a plurality of nano-fingers extending from the exterior surface of the elongated substrate, wherein the plurality of SES elements are positioned on tips of the plurality of nano-fingers.

5. The apparatus according to claim 4, wherein the plurality of nano-fingers are partially collapsed onto adjacent ones of the plurality of nano-fingers such that tips of the adjacent nano-fingers are in close proximities with respect to each other and that the plurality of SES elements on the tips of at least some of the adjacent nano-fingers are in contact with each other.

6. The apparatus according to claim 1, further comprising:
   a cover layer covering the plurality of SES elements.

7. The apparatus according to claim 6, wherein the cover layer is at least one of dissolvable in a fluid, photolyzable, and removable through receipt of an external stimulus.

8. The apparatus according to claim 6, wherein the cover layer comprises a porous membrane that is to substantially prevent certain particles from contacting the plurality of SES elements.

9. The apparatus according to claim 1, wherein a plurality of groups of the plurality of SES elements are positioned on the surface of the elongated substrate at a plurality of distinct locations between the first end and the second end of the elongated substrate.

10. The apparatus according to claim 9, further comprising:
    a first cover layer covering a first group of the plurality of SES elements; and
    a second cover layer covering a second group of the plurality of SES elements;
    wherein the first cover layer and the second cover layer are independently removable with respect to each other.

11. The apparatus according to claim 1, further comprising:
    a drug material provided on the elongated substrate, wherein the drug material is to be introduced into the specimen following at least one of a predetermined amount of time and upon receipt of an external stimulus.

12. A system for performing spectroscopy, said system comprising:
    an elongated substrate having a shape and size to be inserted into a specimen, wherein the elongated substrate has a first end and a second end, and wherein the elongated substrate has a diameter or width that is between about 0.1 mm to about 10 mm; and
    a plurality of surface-enhanced spectroscopy (SES) elements positioned on an exterior surface of the elongated substrate at a location between the first end and the second end of the elongated substrate;
    an illumination source to illuminate the plurality of SES elements; and
    a spectrometer to detect light emitted from an analyte positioned near the plurality of SES elements.

13. The system according to claim 12, wherein the elongated substrate comprises an acupuncture needle.

14. A method for performing spectroscopy, said method comprising:
    inserting at least a portion of an apparatus into a specimen comprising a fluid containing target particles to cause at least some of the target particles to contact the plurality of SES elements, wherein the apparatus includes an elongated substrate having a shape and size to be inserted into a specimen, wherein the elongated substrate has a first end and a second end, and a plurality of surface-enhanced spectroscopy (SES) elements positioned on an exterior surface of the elongated substrate at a location between the first end and the second end of the elongated substrate;
    directing an illumination beam onto the plurality of SES elements and the target particles to cause the target particles to emit scattered signals; and
    measuring the scattered signals emitted by the target particles.

15. The method according to claim 14, wherein the elongated substrate comprises an acupuncture needle and wherein inserting at least a portion of the apparatus into the specimen further comprises inserting at least a portion of the apparatus into the specimen as an acupuncture needle.

* * * * *